United States Patent
Adler et al.

(10) Patent No.: US 12,357,748 B2
(45) Date of Patent: Jul. 15, 2025

(54) MICRODOSING

(71) Applicant: HOFFMANN-LA ROCHE INC., Little Falls, NJ (US)

(72) Inventors: Michael Adler, Basel (CH); Joerg Luemkemann, Basel (CH); Hanns-Christian Mahler, Basel (CH); Denis Luthringer, Basel (CH); Alexander Meyer, Basel (CH); Adeline Boillon, Basel (CH); Anke Dorn, Basel (CH); Karoline Bechthold-Peters, Basel (CH); Tim Dreckmann, Basel (CH); Andreas Ernst, Freiburg (DE)

(73) Assignee: HOFFMANN-LA ROCHE INC., Little Falls, NJ (US)

( * ) Notice: Subject to any disclaimer, the term of this patent is extended or adjusted under 35 U.S.C. 154(b) by 1126 days.

(21) Appl. No.: 17/286,242

(22) PCT Filed: Oct. 18, 2019

(86) PCT No.: PCT/EP2019/078397
§ 371 (c)(1),
(2) Date: Apr. 16, 2021

(87) PCT Pub. No.: WO2020/079236
PCT Pub. Date: Apr. 23, 2020

(65) Prior Publication Data
US 2021/0346598 A1    Nov. 11, 2021

(30) Foreign Application Priority Data

Oct. 19, 2018 (EP) .................... 18201464

(51) Int. Cl.
*A61M 5/142* (2006.01)
*A61M 5/315* (2006.01)
*F04B 43/12* (2006.01)

(52) U.S. Cl.
CPC .... *A61M 5/14228* (2013.01); *A61M 5/31531* (2013.01); *A61M 5/31556* (2013.01);
(Continued)

(58) Field of Classification Search
CPC .......... A61M 5/14228; A61M 5/31531; A61M 5/31556; A61M 2205/3334; F04B 43/12
See application file for complete search history.

(56) References Cited

U.S. PATENT DOCUMENTS

| 4,617,014 A | 10/1986 | Cannon et al. |
| 5,078,683 A | 1/1992 | Sancoff et al. |
| 7,985,198 B2 * | 7/2011 | von Blumenthal ......................... A61M 5/16827 604/890.1 |

(Continued)

FOREIGN PATENT DOCUMENTS

| EP | 0215249 A1 | 3/1987 |
| EP | 2169225 A2 | 3/2010 |

(Continued)

OTHER PUBLICATIONS

Notice of Reasons for Rejection issued Oct. 17, 2023 in corresponding Japan Appl. No. 2021-520552.
(Continued)

*Primary Examiner* — Timothy L Maust
(74) *Attorney, Agent, or Firm* — MEDLER FERRO WOODHOUSE & MILLS PLLC (57) ABSTRACT

A dosing system for transferring an aseptic fluid in dosages into a container, comprising a peristaltic pump configured such that the filling accuracy for fill volumes of the aseptic fluid<100 μL is ±3 μL.

20 Claims, 8 Drawing Sheets

(52) U.S. Cl.
CPC ..... *F04B 43/12* (2013.01); *A61M 2205/0294* (2013.01); *A61M 2205/3334* (2013.01)

(56) References Cited

U.S. PATENT DOCUMENTS

| | | | |
|---|---|---|---|
| 10,350,593 B2* | 7/2019 | Shmilovich | ....... B01L 3/502707 |
| 10,928,236 B2* | 2/2021 | Adler | ....................... G01F 11/00 |
| 2005/0277911 A1 | 12/2005 | Stewart et al. | |
| 2012/0189476 A1 | 7/2012 | Nagel et al. | |
| 2015/0071920 A1 | 3/2015 | Larson et al. | |

FOREIGN PATENT DOCUMENTS

| | | |
|---|---|---|
| EP | 2842586 A1 | 3/2015 |
| JP | 2015-163192 A | 9/2015 |
| JP | 2015163193 A | 9/2015 |
| JP | 2016534141 A | 11/2016 |
| JP | 2016214793 A | 12/2016 |
| JP | 2017521190 A | 8/2017 |
| WO | 2009/137780 A2 | 11/2009 |
| WO | 2011085274 A1 | 7/2011 |
| WO | 2014048911 A1 | 4/2014 |
| WO | 2016012567 A1 | 1/2016 |

OTHER PUBLICATIONS

Notice of Reasons for Rejection issued on Feb. 6, 2024 in corresponding JP patent application No. 2021-520552.

Written Opinion of the International Searching Authority issued Nov. 13, 2019 in corresponding International Patent Application No. PCT/EP2019/078397.

* cited by examiner

MICRODOSING

FIELD OF THE INVENTION

Present invention relates to a process for controlling accuracy of a microdosing system.

BACKGROUND OF THE INVENTION

Pharmaceutical applications fluids may need to be dosed in very small volumes like at volumes of less than 100 μL. Such dosing must often be performed under sterile conditions. Increasing titers and higher concentrated drug product formulations in the pharmaceutical industry lead to such low fill volumes in the range of 50-100 μL[1].

Further, small deviations in dosage should often be prevented for therapeutic reasons. Traditional dosing systems for dosing liquids at comparably small volumes like radial peristaltic pumps and rotary piston pumps lack a dose accuracy and consistency (see Greb et al.[2]) when filling volumes <100 μL or even <50 μL. These traditional dosage systems might even damage the delicate biotech products as they apply a comparably high stress to the liquid, as described by Cromwel et al.[3] or Thomas et al.[4].

A peristaltic pump being capable of gently and precisely dosing a fluid at small volumes is described in WO2016125670[5]. A pressure sensor for measuring a fluid pressure of a fluid within a measurement chamber is described in WO2014048911[6].

There is thus an ongoing need to identify and characterize a dosing system with a reliable in-process control (IPC) for low volume high precision aseptic filling of parenterals.

DISCLOSURE OF THE INVENTION

Present invention relates to a process for controlling accuracy of a microdosing system for fluids using a dosing system comprising a linear peristaltic pump and, advantageously, a sensor for measuring the dispensed volumes. Present invention provides a dosing system with a reliable in-process control for low volume high precision aseptic filling of parenterals using a peristaltic pump and, advantageously, a pressure sensor.

The term "peristaltic" relates to a transverse or radial contraction and relaxation of a hollow flexible longitudinal element such as the flexible tube allowing to propagate a wave along the element.

The term "dosage" as used herein can relate to the provision of an exact predefined amount of the fluid. It can particularly relate to the provision of small volumes of less than (<) 100 microliter (μl or μL) e.g. 50 μl, 30 μl, 20 μl, 12 μl and the like.

The term "±" in connection with a number (x), like x±y includes any the values including x+y, between x+y and x−y and including x−y.

The term "fluid" relates to any substance that continually deforms or flows under an applied shear stress. In particular the term relates to a liquid.

The term "monoclonal antibody" (mAB) are antibodies that are made by identical immune cells that are all clones of a unique parent cell.

The term "aseptic" means free from pathogenic microorganisms.

The term "surfactant" relates to excipients, in particular pharmaceutical excipients, that reduces the surface tension when added to a liquid. They can for example stabilize mAB formulations by preventing protein degradation and aggregation.

The terms "right", "left", "up", "down", "top" and "bottom" as well as their derivations and terms with a similar meaning refer to directions in the figures.

The term "container" as used herein relates to a containment suitable for receiving the aseptic fluid. In particular, the container can be a vial, a syringe or a cartridge.

More specifically, the need of the prior art to identify and characterize a dosing system and process with a reliable in-process control (IPC) for low volume high precision aseptic filling of parenterals is settled by a dosing system as it is defined by the features of independent claim 1, and by a process as it is defined by the features of independent claim 14. Preferred embodiments are subject of the dependent claims.

In one aspect, the invention is a dosing system for transferring an aseptic fluid in dosages into a container. The dosing system comprising a peristaltic pump configured such that the filling accuracy for fill volumes of the aseptic fluid <100 μL is ±3 μL. By providing the dosing system with the peristaltic pump it is possible to achieve the intended dosing accuracy. In particular, it has been found that for filling volumes of less than 100 μL an accuracy of ±3 μL is appropriate for many aseptic fluids.

Preferably, the aseptic fluid is a liquid solution such as a pharmaceutical or drug solution and, more preferably, a liquid mAb solution.

The term "drug" as used herein relates to a therapeutically active agent, also commonly called active pharmaceutical ingredient (API), as well as to a combination of plural such therapeutically active substances. The term also encompasses diagnostic or imaging agents, like for example contrast agents (e.g. MRI contrast agents), tracers (e.g. PET tracers) and hormones, that need to be administered in liquid form to the patient.

The term "drug substance" as used herein relates to a drug as defined above formulated or reconstituted in a form that is suitable for administration to the patient. For example, besides the drug, a drug substance may additionally comprise an excipient and/or other auxiliary ingredients. A particularly preferred drug substance in the context of the invention is a drug solution, in particular a solution for oral administration, injection or infusion.

The term "drug product" as used herein relates to a finished end product comprising a drug substance or a plurality of drug substances. In particular, a drug product may be a ready to use product having the drug substance in an appropriate dosage and/or in an appropriate form for administration. For example, a drug product may include an administration device such as a prefilled syringe or the like.

Preferably, the filling accuracy for fill volumes of the aseptic fluid <50 μL is ±1.5 μL, the filling accuracy for fill volumes of the aseptic fluid <30 μL is ±1.0 μL, the filling accuracy for fill volumes of the aseptic fluid <20 μL is ±0.5 μL, and/or the filling accuracy for fill volumes of the aseptic fluid <12 μL is ±0.05 μL. Particularly when drug solutions or mAb solutions are involved, such accuracy is appropriate for the given fill volumes.

Preferably, the dosing system has surfaces manufactured from a sterilizable material. More specifically, all surfaces of the dosing system being accessible from outside or from the exterior such as the exterior surface of the peristaltic pump advantageously are sterilizable. Like this, the dosing system can efficiently be sterilized to be efficiently applicable for filling the aseptic fluid.

Preferably, the aseptic fluid has a viscosity of <15 cP±2 cP, the aseptic fluid has a viscosity of 16 cP±1 cP, the aseptic fluid has a viscosity of <1500 cP±20 cP, and/or the aseptic fluid has a viscosity of 1480 cP±1 cP. The dosing system can particularly, be suitable for fluids having such viscosity.

The peristaltic pump can be any peristaltic pump suitable for being configured to achieve the defined filling accuracy. For example, the peristaltic pump can be a radial peristaltic pump.

However, preferably the peristaltic pump comprises a flexible tube, a counter pressure element, a plurality of actors and a drive, wherein the flexible tube is arranged along the counter pressure element, the actors are moveable by the drive in relation to the flexible tube, the flexible tube is compressible between the actors and the counter pressure element by moving the actors, the flexible tube is essentially straightly arranged along the counter pressure element thereby forming a longitudinal axis, the actors are arranged parallel to each other along the longitudinal axis of the flexible tube, and each of the actors is independently and linearly moveable by the drive along an actuation axis essentially perpendicular to the longitudinal axis of the flexible tube from a home position in which the flexible tube is open for a fluid to pass to an end position in which the flexible tube is compressed and sealed.

The counter pressure element of the peristaltic pump can be a fixed element having a guidance for the flexible tube. In particular, the flexible tube can be arranged in or along the guidance of the counter pressure element. The guidance can be or comprise a flat surface facing the flexible tube and allowing the latter to be straightly arranged. By arranging the flexible tube in a straight manner the peristaltic pump can be a linear peristaltic pump. When any of the actors act on or push the flexible tube the counter pressure element fixedly stays in its original position such that the flexible tube is compressed in between the actor and the counter pressure element.

The flexible tube can have an inner diameter of about 200 μm to about 1,000 μm, or of about 300 μm to about 900 μm, or about 500 μm to about 800 μm. Such tubes can be suitable for providing dosages with the peristaltic pump at intended volumes.

The actors of the peristaltic pump can be cubical blocks or other similar bodies having a face for acting on the flexible tube. The face can be flat and can have a width in a range 50 micrometer (μm) to 1,000 μm or in a range of 100 μm and 700 μm or in range of 200 μm and 500 μm. The actors can have a maximum stroke, i.e. the length between its home position and its end position, of about 800 μm, or about 600 μm, or about 500 μm, or about 400 μm, or about 300 μm. Such actors can be suitable for providing dosages in the system according to the invention at intended volumes.

The term "compress" as used herein can relate to an elastic deformation of the tube. Particularly, it can relate to elastically moving the side walls of the flexible tube into the direction of each other, i.e. into a transversal or radial direction, thereby narrowing or closing the inner duct of the flexible tube. In this context, the term "seal" can relate to compress the flexible tube to such an extent that essentially no fluid can pass the inner duct of the flexible tube.

In connection to the home position of the actors, the flexible tube is open for the fluid to pass in the sense that the fluid can flow through the inner duct of the flexible tube. This can be best possible in a situation where the respective actuator is moved to a maximum possible distance from the counter pressure element such that the flexible tube is least compressed.

The specific peristaltic pump of the dosing system having linear actuators allows for exactly and repeatably providing dosages at comparably small volumes in a sterile environment. It is particularly suitable to be used in an industrial dosage or filling process line. It can be used for aseptically dosing parenteralia at volumes less than 1 ml such as up to 25 μl or 50 μl or even 10 μl, e.g., in a pharmaceutical filling process. Compared to other peristaltic dosage systems such as radial peristaltic pumps, such peristaltic device can efficiently be configured to achieve the intended filling accuracy for each aimed filling volume. For example, the linear actuators can be very precisely moved such that compression of the tube and, thus, dosing or filling volume can be fine tuned.

Further, since the flexible tube is straightly arranged when being pumped, this peristaltic pump is suitable for fluids having a broad variety of viscosities. Particularly, fluids having a comparably high viscosity such as mAb solutions can also be dosed with the peristaltic pump.

The drive of the peristaltic pump can be a stepper motor or servomotor which allows for precisely advancing or moving the actors. Alternatively, the drive comprises a piezoelectric actuation. Piezoelectric actuation allows for precisely end flexibly moving the actors such that various dosage schemes can be implemented in the peristaltic pump. The arrangement of the drive with the piezoelectric actuation makes it possible that the drive is embodied with comparably few and simple parts. Thus, it can be comparably robust and require comparably low maintenance effort.

The flexible tube preferably is partially pre-compressed between the plurality of actors and the counter pressure element when all actors of the plurality of actors are in their home positions. Such pre-compression allows the flexible tube to be fixed over a substantial length. In particular, it can prevent that the flexible tube is longitudinally moved in a section where the actors are applied. Like this, a precise compression of the flexible tube is possible and stress of the side walls of the flexible tube in a longitudinal direction can be reduced or prevented. Furthermore, such pre-compression allows for predefining and adjusting a filling volume as well as filling accuracy. Thereby, the filling volume can be defined by the inner space of the flexible tube which lies between the actors and the counter pressure element. Beyond others, such adjustment of the filling volume allows for compensating an increasing deviation of the filling volume from its set point, e.g., induced by heating the fluid or softening of the flexible tube or tubing caused by mechanical stress.

Preferably, the dosing system comprises a liquid flow measurement sensor connected to the peristaltic pump configured to report a volume of fluid passed through the peristaltic pump.

Suitable sensors include flow sensors, pressure sensors like capacitive pressure sensors, and optical sensors like camera-based sensor. A particular suitable sensor is a capacitive pressure sensor.

Such sensor allows for providing a feedback as to the filled volume. For example, an electronic signal can be created as feedback. The feedback can then be used to control the peristaltic pump as to its filling volumes. For example, the sensor can provide a feedback about the fill volume and the peristaltic pump is stopped or interrupted when the aimed volume is achieved. Like this, the intended filling accuracy can efficiently be achieved in a fully automatic manner. In particular, the capacitive pressure sensor allows for providing a comparably quick feedback such that the filling volume can more or less be determined in run time. Like this, a specifically advanced filling accuracy can be achieved. In particular, when being combined with a peristaltic pump having linear actuators as explained above, the quick feedback of the sensor can quickly, reliably and precisely be effectuated by the movement of the actuators such that the filling volume can be defined.

For differential capacitive pressure measurement, the dosing system can comprise two similar or identical sensors such as capacitive pressure sensors. Such dosing system allows for setting-up with a fluidic resistance in between the two sensors, so that any flow through the fluidic resistance changes the pressure difference before and after the resistance. Measured can be the signal of the pressure sensors whose capacitance is changing due to mechanical expansion of the tube in between the electrodes. Such arrangement allows for a particularly accurate and efficient determination of the effectuated filling volume.

For relative capacitive pressure measurement, a single sensor can be placed on one side of the fluidic resistance while ambient pressure on the other side of the resistance throughout the dispensing procedure is assured A relative change of the pressure in the sensor caused by a flow through the fluidic resistance is measured.

For controlling the peristaltic pump, the dosing system can comprise a control unit which is adapted to control the compression-force acting on the flexible tube. The control unit can be adapted to adjust the length of the path of the actuators, for example, by adjusting the pre-compression of the flexible tube of the peristaltic pump. With such a force control the dosage amount of fluid can precisely kept on a constant level over the time. In particular, changes of the properties of the material of the flexible tube over the time can be compensated. For example, over the time the material of the flexible tube can be worn by the mechanical stress of the milking movements of the actuators. In such a situation the rate of compression can decrease. By increasing the path of the actuators by adjusting the pre-compression of the flexible tube such decrease can be compensated such that the force can be kept constant. Also, such control unit allows for efficiently evaluating the feedback of the sensor such that a comparably high filling accuracy can be achieved.

Preferably, the dosing system comprises a control unit coupled or connected to the peristaltic pump and coupled or connected to the liquid flow measurement sensor, wherein the control unit is configured to receive a data signal from the liquid flow measurement sensor, to evaluate the received data signal, and to adapt the peristaltic pump in accordance with the evaluated data signal. Such control unit allows for efficiently controlling the dosing system and particularly its peristaltic pump in a fully automated fashion.

Thereby, adapting the peristaltic pump preferably comprises adjusting a volume dispensed by the peristaltic pump. For example, the adjusted volume can be the volume of one dosage provided by the peristaltic pump. More specifically, adjusting the volume can include changing the amount of movement of the actuator(s) of the peristaltic pump, varying the pre-tensioning of the tube of the peristaltic pump in order to reduce or enlarge the inner space of the tube at the peristaltic pump, and/or specifying a number of cycles of actuation per dispensed volume or dosage.

In another aspect, the invention is a process for controlling the accuracy of a dosing system as described above, wherein a dispensed volume of the aseptic fluid by a peristaltic pump is measured by a liquid flow measurement sensor connected to the peristaltic pump for reporting a volume of a fluid passed through the peristaltic pump.

Such process and its preferred embodiments described below allow for efficiently achieving the effects and benefits of the dosing system and its preferred embodiments described above.

Preferably, in the process the sensor measures the change of capacitance in the orifice of the capacitor, when a fluid is between the electrodes compared to the capacitance of air.

Preferably, the volume of 50 µL±3 µL is dispensed according to the following settings: 6±1 cycles, in particular 2±1 cycles, and 30 Hz±10 piezo frequency, in particular 30 Hz±1 piezo frequency. Such settings allow for efficiently achieving an appropriate filling accuracy at the intended filling volumes.

Preferably, the process involves a tubing between ID=1.6-0.8 mm, in particular 1.6 or 0.8 mm. Thereby, the abbreviation ID relates to the internal diameter of the tubing. The tubing can be comprised by the dosing system and can, particularly, be the flexible tube of the peristaltic pump.

Preferably, the process involves a tubing with a wall thickness of 1.6 mm. Again, the tubing can be comprised by the dosing system and can, particularly, be the flexible tube of the peristaltic pump.

Preferably, the peristaltic pump is controlled in accordance with the volume of the fluid reported by the liquid flow measurement sensor. In particular, the liquid flow measurement sensor can provide a data signal representing the volume of the fluid measured. This data signal can be transferred to a control unit which evaluates the data signal and adjusts settings of the peristaltic pump in accordance with the evaluated data signal.

Thereby, controlling the peristaltic pump preferably comprises adjusting a volume dispensed by the peristaltic pump.

Further embodiments of the present disclosure are listed in the following:

E1: A dosing system for transferring an aseptic fluid in dosages, in particular wherein the aseptic fluid is a liquid solution, in particular a liquid mAbs solution, wherein the filling accuracy for fill volumes of the fluid <100 µL is ±3 µL, in particular wherein the filling accuracy for fill volumes of <50 µL is ±1.5 µL.

E2: A dosing system as described herein for transferring an aseptic fluid in dosages, in particular wherein the aseptic fluid is a liquid mAbs solution.

E3: A dosing system as described herein for transferring an aseptic mAbs solution in dosages.

E4: A dosing system as described herein, wherein the aseptic fluid contains a surfactant.

E5: A dosing system for transferring an aseptic fluid in dosages

E6: A dosing system for transferring an aseptic fluid in dosages, in particular wherein the aseptic fluid is a liquid solution, in particular a liquid mAbs solution, wherein the filling accuracy for fill volumes of the fluid <100 µL is ±3 µL.

E7: A dosing system for transferring an aseptic fluid in dosages, in particular wherein the aseptic fluid is a liquid solution, in particular a liquid mAbs solution, wherein the filling accuracy for fill volumes of <50 µL is ±1.5 µL.

E8: A dosing system for transferring an aseptic fluid in dosages, in particular wherein the aseptic fluid is a liquid solution, in particular a liquid mAbs solution, wherein the filling accuracy for fill volumes between 100-20 µL is ±1.0 µL.

E9: A dosing system as described herein, wherein the filling accuracy for fill volumes of the aseptic fluid <30 µL is ±1.0 µL, in particular wherein the filling accuracy for fill volumes of the fluid <20 µL is ±0.5 µL.

E10: A dosing system as described herein, wherein the filling accuracy for fill volumes of the aseptic fluid <30 µL is ±1.0 µL.

E11: A dosing system as described herein, wherein the filling accuracy for fill volumes of the aseptic fluid <20 µL is ±0.5 µL.

E12: A dosing system as described herein, wherein the filling accuracy for fill volumes of the aseptic fluid <12 µL is ±0.05 µL.

E13: A dosing system as described herein having surfaces manufactured from a sterilizable material.

E14: A dosing system as described herein, wherein the aseptic fluid has a viscosity between 1500 and 15 cP.

E15: A dosing system as described herein, wherein the aseptic fluid has a viscosity of <15 cP±2 cP, in particular 16 cP±1 cP.

E16: A dosing system as described herein, wherein the aseptic fluid has a viscosity of <15 cP±2 cP.

E17: A dosing system as described herein, wherein the aseptic fluid has a viscosity of 16 cP±1 cP.

E18: A dosing system as described herein, wherein the aseptic fluid has a viscosity of 16 cP.

E19: A dosing system as described herein, wherein the aseptic fluid has a viscosity of <1500 cP±20 cP, in particular 1480 cP±1 cP.

E20: A dosing system as described herein, wherein the aseptic fluid has a viscosity of <1500 cP±20 cP.

E21: A dosing system as described herein, wherein the aseptic fluid has a viscosity of 1480 cP±1 cP.

E22: A dosing system as described herein, wherein the aseptic fluid has a viscosity of 1480 cP.

E23: A dosing system as described herein, wherein the peristaltic pump (1; 18; 19) comprises a flexible tube (13; 138; 139), a counter pressure element (12; 128; 129), a plurality of actors (11; 118; 119) and a drive (17; 178; 179), wherein
  the flexible tube (13; 138; 139) is arranged along the counter pressure element,
  the actors (11; 118; 119) are moveable by the drive (17; 178; 179) in relation to the flexible tube (13; 138; 139), and
  the flexible tube (13; 138; 139) is compressible between the actors (11; 118; 119) and the counter pressure element (12; 128; 129) by moving the actors (11; 118; 119),
  the flexible tube (13; 138; 139) is essentially straightly arranged along the counter pressure element (12; 128; 129) thereby forming a longitudinal axis,
  the actors (11; 118; 119) are arranged parallel to each other along the longitudinal axis of the flexible tube (13; 138; 139), and
  each of the actors (11; 118; 119) is independently and linearly moveable by the drive (17; 178; 179) along an actuation axis essentially perpendicular to the longitudinal axis of the flexible tube (13; 138; 139) from a home position in which the flexible tube (13; 138; 139) is open for a fluid to pass to an end position in which the flexible tube (13; 138; 139) is compressed and sealed, and
  the flexible tube (13; 138; 139) is partially pre-compressed between the plurality of actors (11; 118; 119) and the counter pressure element (12; 128; 129) when all actors (11; 118; 119) of the plurality of actors (11; 118; 119) are in their home positions.

E24: A dosing system as described herein, wherein the peristaltic pump as described herein, comprises a piezoelectric actuation.

E25: A dosing system as described herein, wherein the peristaltic pump as described herein, wherein the plurality of actors (11; 118; 119) is a series of three to fifteen or five to thirteen or seven to eleven parallel actors (11; 118; 119).

E26: A dosing system as described herein, wherein the peristaltic pump as described herein, comprising a tube fixation structure (14) for releasably fixing the flexible tube (13; 138; 139) in the essentially straight position along the counter pressure element (12; 128; 129).

E27: A dosing system as described herein, wherein the peristaltic pump as described herein, wherein the tube fixation structure (14) comprises an extension jacket (14) wherein one of the longitudinal ends of the flexible tube (13; 138; 139) is fixed in the extension jacket (14).

E28: A dosing system as described herein, wherein the peristaltic pump as described herein, wherein the flexible tube (13; 138; 139) is manufactured from a disposable material.

E29: A dosing system as described herein, wherein the peristaltic pump as described herein, comprising a fluid reservoir (188; 189) connected to one of the longitudinal ends of the flexible tube (13; 138; 139) and a filling needle (15; 158; 159) connected to the other one of the longitudinal ends of the flexible tube (13; 138; 139).

E30: A dosing system as described herein, wherein the peristaltic pump as described herein comprises a filling apparatus (2) for automatically filling containers with dosages of a fluid at a volume of less than one milliliter, comprising
  a container holder in which a number of containers is arrangeable for being filled,
  a set of peristaltic pumps (1; 18; 19) as described herein and
  a dosing system positioner arranged to position the set of peristaltic pumps such that each peristaltic pump (1; 18; 19) of the set of peristaltic pumps (1; 18; 19) is arranged adjacent to one of the number of containers arranged in the container holder for filling the number of containers and to remove the set of peristaltic pumps (1; 18; 19) from the container holder.

E31: A dosing system as described herein, wherein the peristaltic pump as described herein, wherein the filling apparatus according to claim 9 or 10, comprising a conveyor for conveying the container holder along a line, wherein the pump (1; 18; 19) positioner is arranged to convey the set of peristaltic pumps adjacent to the container holder when each peristaltic pump (1; 18; 19) of the set of peristaltic pumps (1; 18; 19) is positioned adjacent to one of the number of containers arranged in the container holder.

E32: A dosing system as described herein, having a tubing between ID=1.6-0.8 mm.

E33: A dosing system as described herein, having a tubing of ID=1.6 mm.

E34: A dosing system as described herein, having a tubing of ID=0.8 mm.

E35: A dosing system as described herein, having a tubing with wall thickness of 1.6 mm.

E36: A dosing system as described herein, comprising a reservoir, a linear peristaltic pump and a dispensing needle, connected by tubes.

E37: A process for controlling the accuracy of a dosing system as described herein, wherein a dispensed volume of the aseptic fluid by a peristaltic pump is measured by a liquid flow measurement sensor connected to the peristaltic pump for reporting a volume of a fluid passed through the pump.

E38: A process for controlling the accuracy of a dosing system as described herein, wherein the sensor is a pressure sensor.

E39: A process for controlling the accuracy of a dosing system as described herein, wherein the sensor is a capacitive pressure sensor.

E40: A process for controlling the accuracy of a dosing system as described herein, wherein the sensor measures the change of capacitance in the orifice of the capacitor, when a fluid is between the electrodes compared to the capacitance of air (FIG. 7,A).

E41: A process for controlling the accuracy of a dosing system as described herein, wherein the sensor is installed at the orifice of the dispensing needle and therewith measuring the volume which was actually released from the dispensing needle.

E42: A process for controlling the accuracy of a dosing system as described herein, using a single pressure sensor.

E43: A process for controlling the accuracy of a dosing system as described herein, using the dispensing needle as fluidic resistance.

E44: A process for controlling the accuracy of a dosing system as described herein, wherein the volume of 50 µL±3 µL is dispensed according to the following settings:
  6±1 cycles, in particular 2±1 cycles,
  30 Hz±10 piezo frequency, in particular 30 Hz±1 piezo frequency.

E45: A process for controlling the accuracy of a dosing system as described herein, wherein the volume of 50 µL±3 µL is dispensed in 6±1 cycles.

E46: A process for controlling the accuracy of a dosing system as described herein, wherein the volume of 50 µL±3 µL is dispensed in 6 cycles.

E47: A process for controlling the accuracy of a dosing system as described herein, wherein the volume of 50 µL±3 µL is dispensed in 2±1 cycles.

E48: A process for controlling the accuracy of a dosing system as described herein, wherein the volume of 50 µL±3 µL is dispensed in 2 cycles.

E49: A process for controlling the accuracy of a dosing system as described herein, wherein the volume of 50 µL±3 µL is dispensed in 1 cycle.

E50: A process for controlling the accuracy of a dosing system as described herein, wherein the volume of 50 µL±3 µL is dispensed at 30 Hz±10 piezo frequency.

E51: A process for controlling the accuracy of a dosing system as described herein, wherein the volume of 50 µL±3 µL is dispensed at 30 Hz±1 piezo frequency.

E52: A process for controlling the accuracy of a dosing system as described herein, wherein the volume of 50 µL±3 µL is dispensed at 30 Hz piezo frequency.

E53: A process for controlling the accuracy of a dosing system as described herein, with radial pump filling.

E54: A process for controlling the accuracy of a dosing system as described herein, with linear peristaltic pump filling.

BRIEF DESCRIPTION OF THE DRAWINGS

FIG. 7 A sensor concept of a reliable in-process control method for low fill volumes, FIG. 8 Dosing accuracy of 3×50 single doses, the upper line of measuring points shows the accuracy of degassed water, the lower line of measuring points the accuracy for a high-viscous model glycerol-water solution (16.49 cP), FIG. 9 Linearity of the fill volume range for two different tubings. Triangles show the volume range for a Tubing with ID=1.6 mm and a wall thickness of 1.6 mm. Squares show the volume range for a Tubing with ID=0.8 mm and a wall thickness of 1.6 mm, FIG. 10 Comparison of different pumps. Two different liquid fluids were recirculated up to 15 times in three different pumps. Dark grey columns represent a liquid fluid without surfactant while the light-grey columns represent a liquid fluid with surfactant. Highest particle counts were found after piston pump recirculation. Radial peristaltic pump filling resulted in higher subvisible particle counts than linear peristaltic pump filling.

DESCRIPTION OF EMBODIMENTS

In the following description certain terms are used for reasons of convenience and are not to be interpreted as limiting. The terms "right", "left", "up", "down", "top" and "bottom" refer to directions in the figures. The terminology comprises the explicitly mentioned terms as well as their derivations and terms with a similar meaning.

Figure 1:
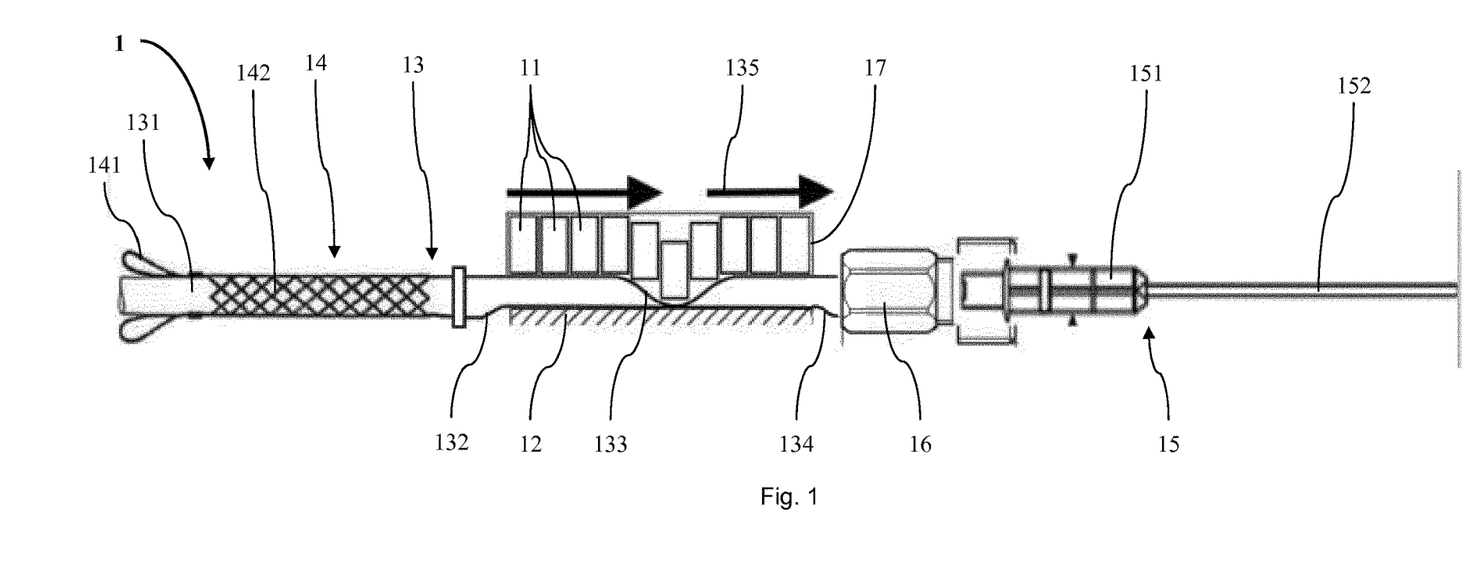
FIG. 1 A schematic view of a first embodiment of a peristaltic pump.

FIG. 1 shows a first embodiment of a linear peristaltic pump 1 of a dosing system according to the invention. In addition to the peristaltic pump 1, the dosing system comprises a control unit 26 and a capacitive pressure sensor 27 as described below in connection with FIG. 7. The peristaltic pump 1 comprises a flexible tube 13, a tube extension jacket 14 as tube fixation structure, a counter pressure plate 12 as counter pressure element, a set of ten parallel piezoelectric actors 11, a dispensing needle 15 as filling needle and a piezoelectric drive unit 17 housing the actors 11 as drive. The tube extension jacket 14 has two straps 141 and a tubular net portion 142. A fixation section 131 of the flexible tube 13 projects through the net portion 142 of the tube extension jacket 14. On expanding the net portion 142, e.g. by pulling the straps 141, it narrows its interior and fixes the flexible tube 13.

Following the tube extension jacket 14 to the right the flexible tube 13 passes on in between a flat surface of the counter pressure plate 12 and actuation faces of the actors 11. The flat surface of the counter pressure plate 12 forms a guidance along which the flexible tube 13 is straightly arranged. Thus, the flexible tube 13 has a longitudinal axis extending in a longitudinal direction 135 which is identical to the direction of advancing the fluid. The counter pressure plate 12 is fixedly or immovably arranged relative to the flexible tube 13, the dispensing needle 15 and the drive unit 17.

The actors 11 are adjacently arranged in parallel such that their actuation faces constitute an essentially continuous front face directed to the flexible tube 13. The piezoelectric drive unit 17 can linearly move each of the actors 11 independently from each other in a stroke direction which is perpendicular to the longitudinal direction 135. The flexible tube 13 is pre-compressed in between the counter pressure plate 12 and the actors 11. For that reason, it has a narrowing section 132 between the tube extension jacket 14 and the counter pressure plate 12 and a widening section 134 between the counter pressure plate 12 and a cap nut 16 following the counter pressure plate 12 to the right. Like this, the flexible tube 13 is clamped and fixedly aligned with regard to the counter pressure plate 12 and the actors 11.

In FIG. 1 the four leftmost actors 11 and the three rightmost actors 11 are in a home position in which they are at a maximum distance to the counter pressure plate 12. The sixth actor 11 counted from the left which is the fifth actor 11 counted from the right is moved by the drive unit 17 into its end position in which a side of the wall of the flexible tube 13 contacting the actors 11 is transversally or radially pressed onto a side of the wall of the flexible tube 13 contacting the counter pressure plate 12. Thereby, the flexible tube 13 is elastically compressed and its inner duct is sealed such that so fluid can pass the actors 11. The two actors 11 neighboring the actor 11 which is in its end position are moved by the drive unit 17 in a position between their home positions and their end positions. Thereby, the moved actors induce a wave portion 133 on the flexible tube 13.

The widening section 134 of the flexible tube 13 passes over into the dispensing needle 15 which is fixed to the piezoelectric drive unit 17 and the counter pressure plate 12 via the cap nut 16. The dispensing needle 15 has a proximal or left-hand body portion 151 and a distal or right-hand pipe portion 152.

In use, the peristaltic pump 1 of the dosing system can be operated in two modes or schemes for providing dosages of the fluid out of the open end of the pipe portion 152 of the dispensing needle 15. In a first path control mode, the actors 11 are identically moved one after the other. In a first step the leftmost actor 11 is moved to its end position and the right side neighboring actor 11 is partially moved into the direction of its end position. All the other actors 11 are in their home positions. In a second step the second leftmost actor 11 is moved to its end position and the two neighboring actors 11 are partially moved into the direction of their end position. All the other actors 11 are in their home positions. In a third step the third leftmost actor 11 is moved to its end position and the two neighboring actors 11 are partially moved into the direction of their end position. All the other actors 11 are in their home positions. This stepwise moving of the actors 11 is continued until in a tenth step the rightmost actor 11 is moved to its end position and the left side neighboring actor 11 is partially moved into the direction of its end position. All the other actors 11 are in their home positions. After the tenth step the process is restarted with the first step.

By moving the actors as described hereinbefore, a wave is generated in the side wall of the flexible tube 13. This wave pushes an exactly predefined volume of the fluid forward into the longitudinal direction 135 to the right. Thereby, the predefined volume of the fluid passes the dispensing needle 15 and exits the open end of the pipe portion 152. The overall volume of one single dosage can be defined by the number of cycles of generating the wave with the actors 11. It can also be less than one full cycle by running plural offset cycles at the same time.

In a second time-pressure control mode of operating the peristaltic pump 1, one or plural actors 11 are moved into the end position thereby sealing the flexible tube 13. Upstream the actors 11, the fluid is set under pressure. By moving the one or plural actors 11 back into the home position, the fluid is advanced by the overpressure into the longitudinal direction 135 to the right and out of the open end of the pipe portion 152 of the dispensing needle 15. After a specific time the one or plural actors 11 are moved again in the end position and the flexible tube 13 is sealed again.

In the time-pressure mode, the dispensed volume is predefined by the time the flexible tube 13 is open and by the pressure in the fluid upstream the actors 11. In a given diameter of the flexible tube 13, the higher the pressure and/or the longer the time are the larger the dispensed volume of fluid is.

In the control unit 26 various parameters of operation of the dosing system and, in particular of its peristaltic pump 1 can be set. General parameters of operation can comprise: number of actors 11, wave speed corresponding to the speed the steps of the actors 11 are advanced and dimension of the wave depending on the number and stroke of simultaneously moved actors 11, e.g. in percent of the path between home position and end position. Parameters specific for the path control mode can comprise: the path length the wave has to travel which, e.g., can be between 0.1 millimeter (mm) and 1,000 mm, the time in which the wave travels the path lengths which, e.g., can be between 1 millisecond (ms) and 10,000 ms. Parameter specific for the time-pressure mode can comprise: identification of the actor(s) 11 sealing the flexible tube, time the flexible tube 13 is opened for one single dosage and pressure of the fluid upstream the actors 11. The control unit 26 monitors the parameters and controls the pressure and the actors 11 via the drive unit accordingly.

Figure 2:
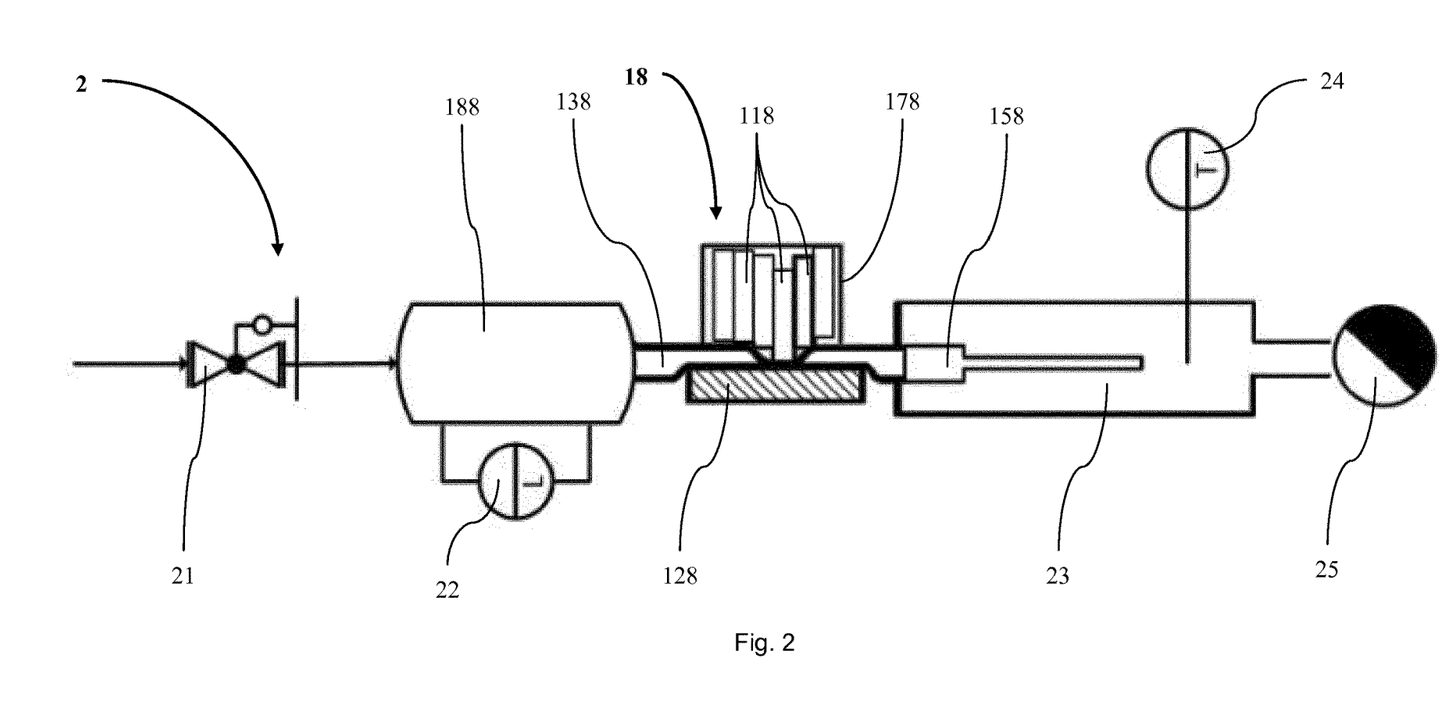
FIG. 2 A schematic view of a dosing system comprising a peristaltic pump.

In FIG. 2 an embodiment of a dosing system 2 according to the invention having a second embodiment of a peristaltic pump 18 is shown. In addition to the peristaltic pump 18, the dosing system 2 comprises a control unit 26 and a capacitive pressure sensor 27 as described below in connection with FIG. 7. The peristaltic pump 18 is similarly embodied as the peristaltic pump 1 shown in FIG. 1. It has a dispensing needle 158, a flexible tube 138, a counter pressure plate 128 as counter pressure element and a piezoelectric drive unit 178 housing six parallel piezoelectric actors 118 as drive. The peristaltic pump 18 further comprises a tank 188 as fluid reservoir being connected to a right hand or upstream end of the flexible tube 138.

The dosing system 2 further comprises a pressure regulator 21 being connected to the tank 188. By means of the pressure regulator 21 a pressure of the fluid inside the tank 188 can be adjusted. The tank 188 is connected to a level sensor 22 sensing a filling level of the tank 188. By means of the level sensor 22 a fluid level of the tank 188 can be monitored and controlled by the control unit 26.

The dispensing needle 158 is positioned inside a needle container 23 to which a temperature gauge 24 and a condensation trap 25 are connected. By means of the needle container 23 a pressurizeable unit is built for steam sterilization. Thereby, clean steam, e.g. of a temperature above 121° C., can pass through the complete fluid path of the filling apparatus 2 for killing life microorganisms from the tank 188 to a open end of the dispensing needle 158. After leaving the dispensing needle 158, the stem fills the needle container 158 and also sterilizes the outer surface of the dispensing needle 158. Condensate that is developing from the steam is drained away from the needle container 23 towards the condensate trap 25 and discarded there. Like this, it can be made sure by applying the steam that a pressure of two bar is built up such that satisfactory sterilization conditions can be provided, e.g. over a time of fifteen minutes.

The dosing system 2 also comprises a vial holder as container holder and a linear robot as dosing system positioner. The linear robot is arranged to position the needle container 23 together with the peristaltic pump 18 adjacent to a vial held by the vial holder. Like this, the linear robot allows to bring a point of dose close to a point of fill which makes a very precise filling or dosing possible.

Figure 3:
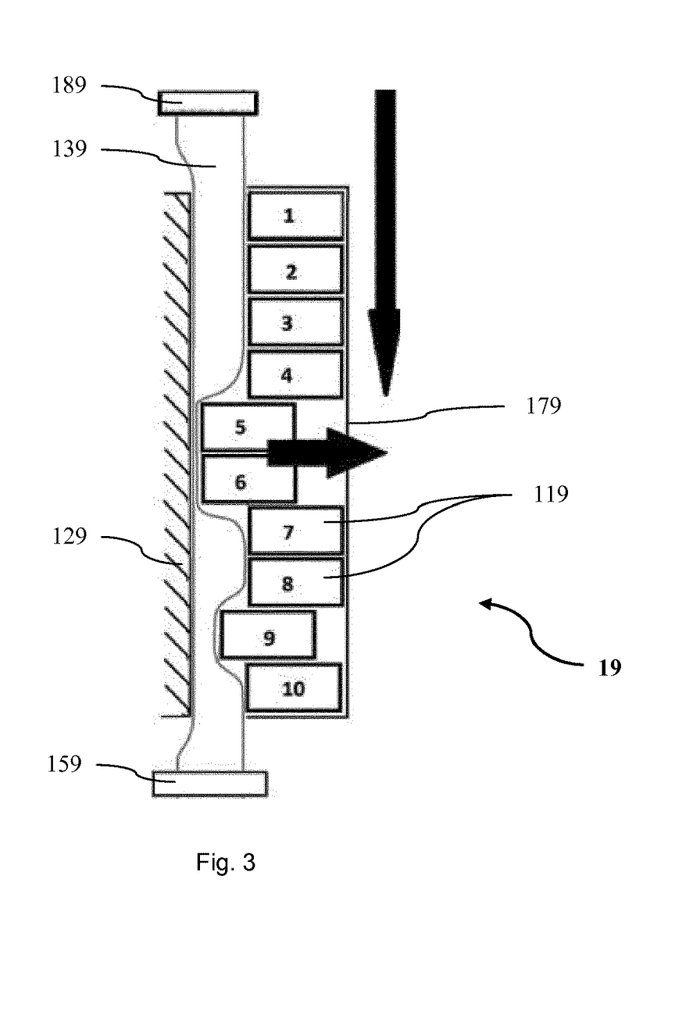
FIG. 3 A schematic view of a peristaltic pump in a first state within a process.

FIG. 3 shows a third embodiment of a peristaltic pump 19 of a dosing system according to the invention being operated in an embodiment of a process according to the invention. The peristaltic pump 19 is similarly embodied as the peristaltic pump 1 shown in FIG. 1 and the peristaltic pump 18 shown in FIG. 2. In a downstream or top-down direction the peristaltic pump 19 comprises a fluid reservoir 189 being connected to a top longitudinal end of a flexible tube 139. The reservoir 189 holds a fluid to dose at an elevated pressure. The flexible tube 139 extends between a counter pressure plate 129 and a ten parallel actors 119, wherein the flexible tube 139 is pre-compressed between the counter pressure plate 129 and the actors 119. The ten actors are housed in a piezoelectric drive unit 179. At its bottom or downstream longitudinal end the flexible tube 139 is connected to a dispensing needle 159. The ten actors 119 are numbered in FIG. 1 from top or upstream first actor 119 to bottom or downstream tenth actor 119.

In FIG. 3 the peristaltic pump 19 is shown in an early stage of the process in which the fifth and the sixth actors 119 are moved by the piezoelectric drive unit 179 into their end positions. Thereby, these two actors 119 seal the flexible tube 139 such that, as indicated by the top arrow, the fluid can only advance up to the fifth actor 11. Additionally, the ninth actor 119 is moved by the drive unit 179 into an intermediate position which lies in between the home and end positions. In the intermediate position the ninth actor 119 slightly compresses the flexible tube 139 without preventing that fluid can pass.

The following applies to the rest of this description. If, in order to clarify the drawings, a figure contains reference signs which are not explained in the directly associated part of the description, then it is referred to previous description sections.

Figure 4:
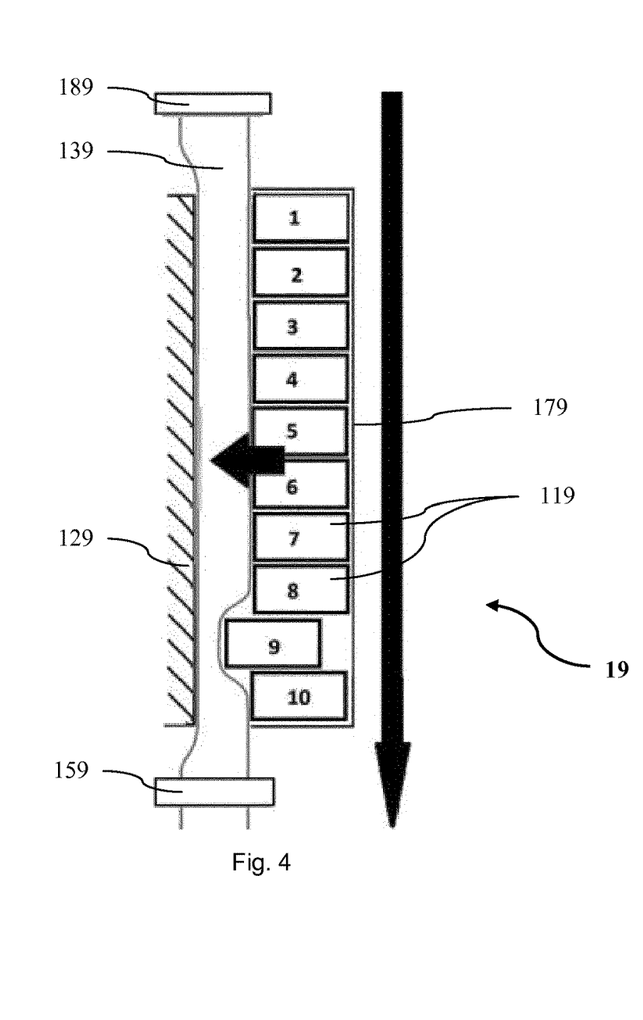
FIG. 4 A schematic view of the peristaltic pump of FIG. 3 in a second state within the process of FIG. 3.

FIG. 4 shows the peristaltic pump 19 in a following stage of the process. Compared to the early stage shown in FIG. 3 the fifth and sixth actors 119 are moved into their home positions by the drive unit 179. The ninth actor 11 still is in its intermediate position. This allows the pressurized fluid to pass through the flexible tube 139 and the dispensing needle 159 into a container to be filled as indicated by the right hand arrow. The peristaltic pump 19 is operated in a time-pressure mode as explained hereinbefore.

Figure 5:
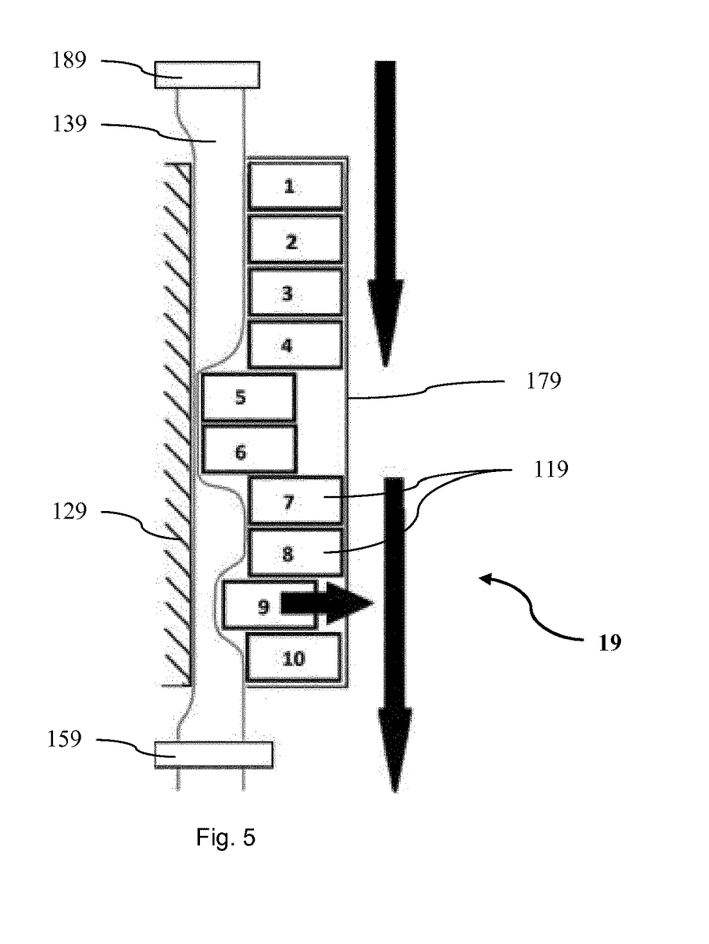
FIG. 5 A schematic view of the peristaltic pump of FIG. 3 in a third state within the process of FIG. 3.

As shown in FIG. 5, after a predefined time allowing a predefined amount of the fluid to be dispensed out of the dispensing needle 159, the fifth and the sixth actors 119 are moved into their end positions again. The ninth actor 11 still is in its intermediate position. Thereby, the flexible tube 139 is sealed again and the fluid may only advance up to the fifth actor 119.

Figure 6:
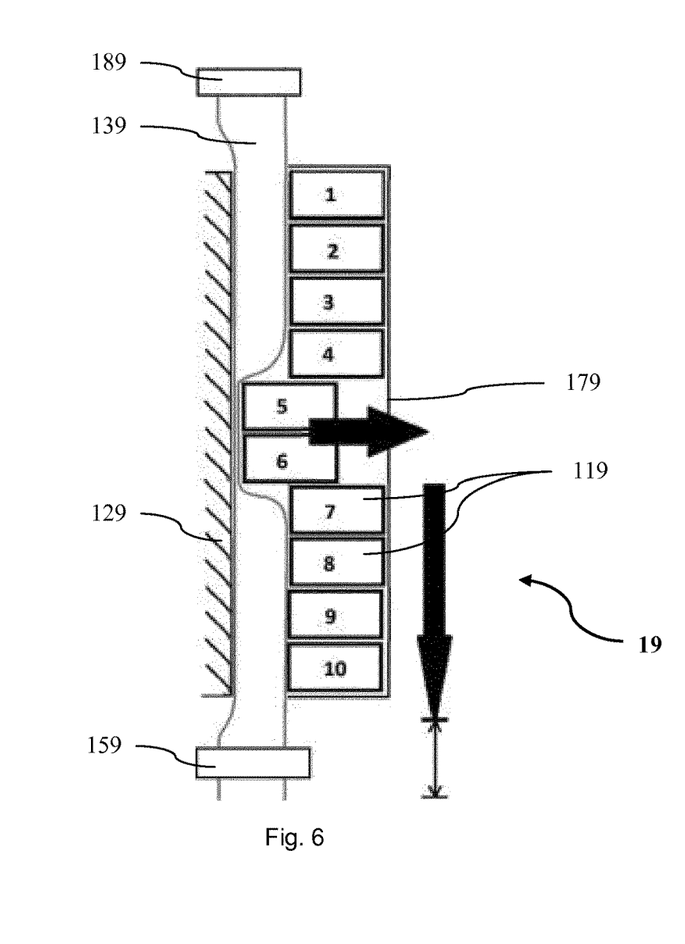
FIG. 6 A schematic view of the peristaltic pump of FIG. 3 in a fourth state within the process of FIG. 3.

In FIG. 6 the peristaltic pump 19 is shown in a further stage of the process. In this stage the ninth actor 119 is moved back into its home position by the drive unit 117. The fifth and sixth actors 119 still are in their end positions sealing the flexible tube 139. By moving the ninth actor back a negative pressure is induced in the lower part of the flexible tube 139. This results in a back sucking effect in the lower part of the flexible tube 139 which allows for preventing leakage and loss of fluid. For providing a next dosage of the fluid the process is repeated.

Figure 7A:
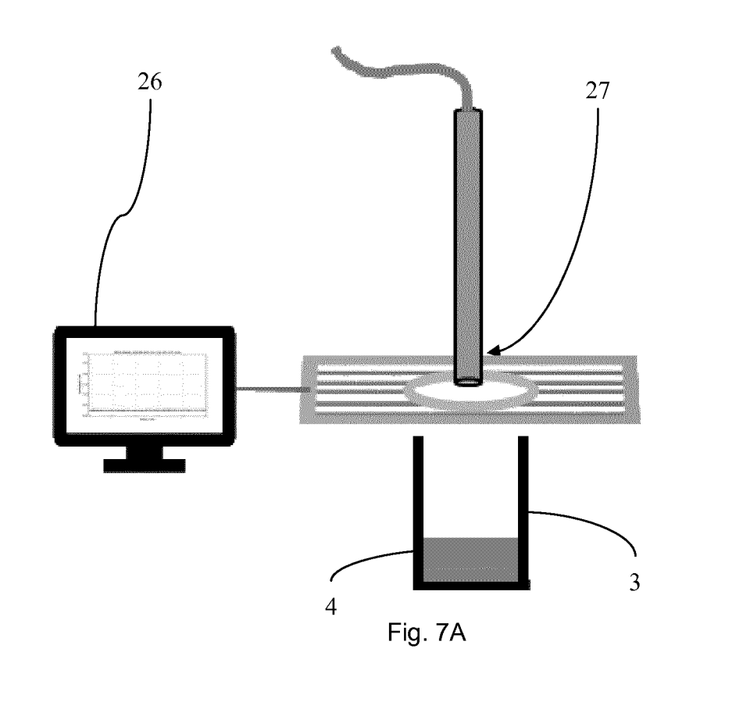
Figure 7B:
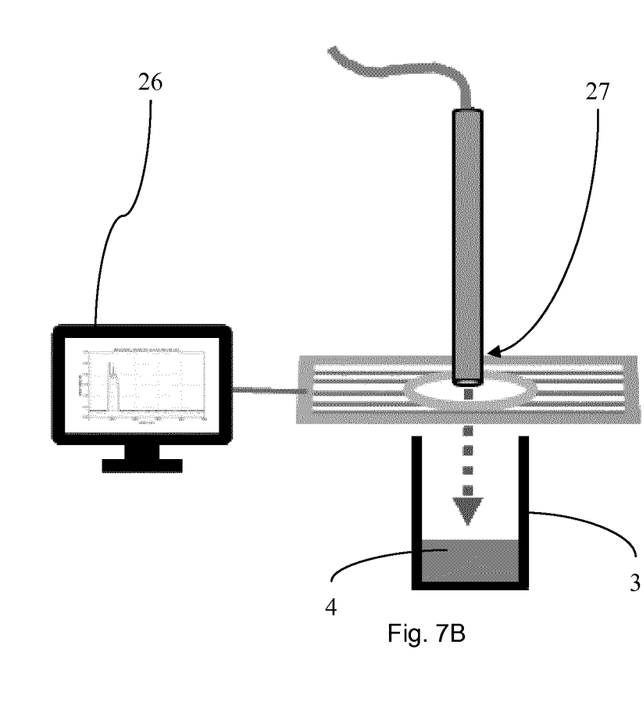
Figure 8:
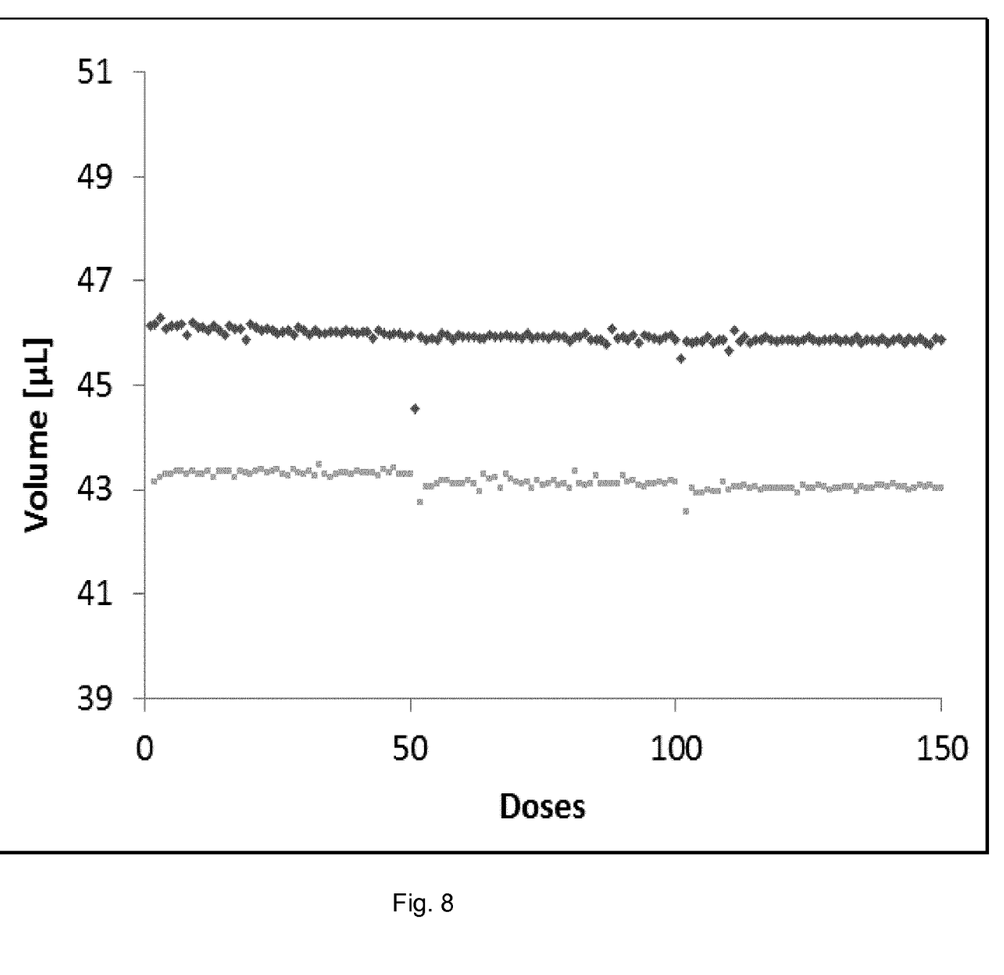
Figure 9:
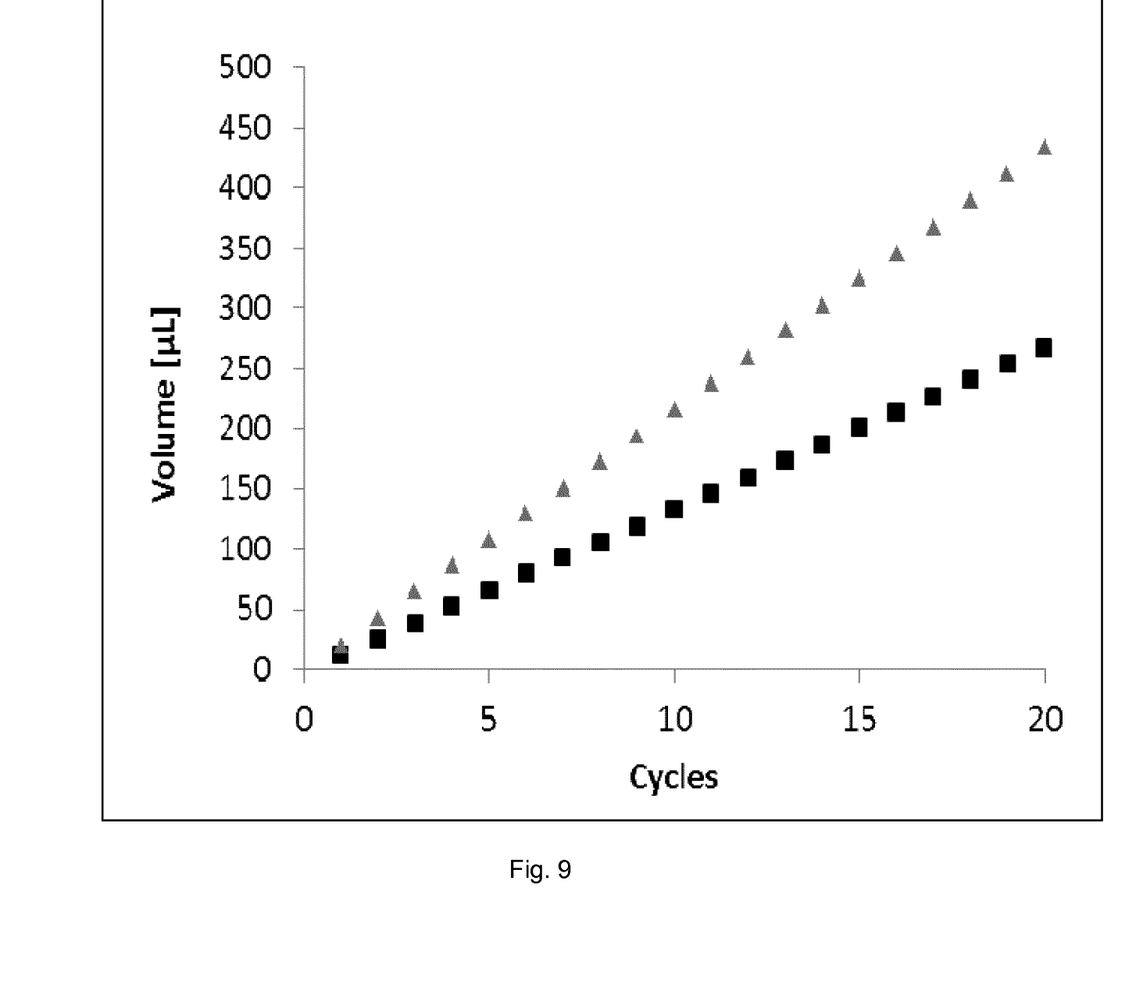
Figure 10:
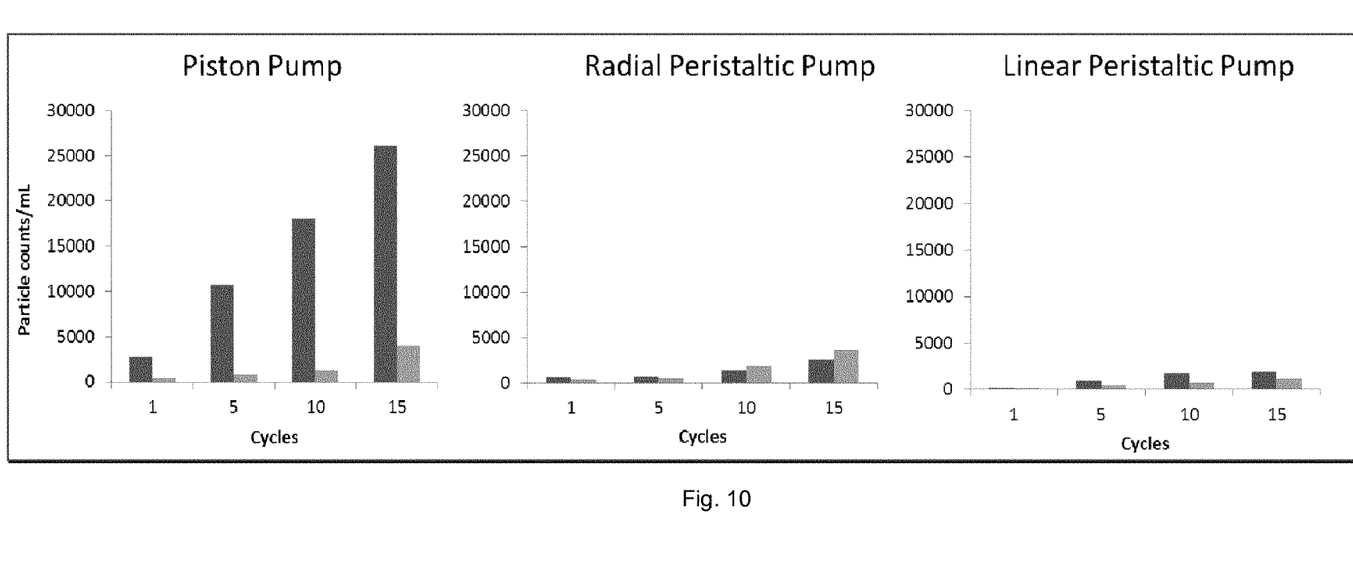

FIG. 7 shows the control unit 26 and the capacitive pressure sensor 27 of the dosing systems described in FIGS. 1 to 6. More specifically, FIG. 7A shows the control unit 26 and the capacitive pressure sensor 27 prior being operated and FIG. 7B shows the control unit 26 and the capacitive pressure sensor 27 while being operated.

The capacitive pressure sensor 27 is directed towards a vial 3 as container which is filled with a mAb solution 4 as aseptic fluid. Further, the capacitive sensor 27 is connected to the control unit 26 by a data communication cable. The capacitive sensor 27 provides a data signal to the control unit 26 as feedback with regard to the volume of the mAb solution 4 filled into the vial 3. The control unit 26 uses the feedback to control the peristaltic pump 1, 18, 19 as to its filling volumes.

For controlling the peristaltic pump 1, 18, 19, the control unit 26 controls the compression force acting on the flexible tube 13, 138, 139. Thereby, the control unit 26 adjusts the length of the path of the actuators 11, 118, 119 by adjusting the pre-compression of the flexible tube 13, 138, 139. With such a force control the dosage amount of fluid is precisely kept on a constant level over the time.

While the invention has been illustrated and described in detail in the drawings and foregoing description, such illustration and description are to be considered illustrative or exemplary and not restrictive. It will be understood that changes and modifications may be made by those of ordinary skill within the scope and spirit of the following claims. In particular, the present invention covers further embodiments with any combination of features from different embodiments described above and below.

The invention also covers all further features shown in the Figs. individually although they may not have been described in the afore or following description. Also, single alternatives of the embodiments described in the figures and the description and single alternatives of features thereof can be disclaimed from the subject matter of the invention or from disclosed subject matter. The disclosure comprises subject matter consisting of the features defined in the claims ort the exemplary embodiments as well as subject matter comprising said features.

Furthermore, in the claims the word "comprising" does not exclude other elements or steps, and the indefinite article "a" or "an" does not exclude a plurality. A single unit or step may fulfill the functions of several features recited in the claims. The mere fact that certain measures are recited in mutually different dependent claims does not indicate that a combination of these measures cannot be used to advantage. The terms "essentially", "about", "approximately" and the like in connection with an attribute or a value particularly also define exactly the attribute or exactly the value, respectively. The term "about" in the context of a given numerate value or range refers to a value or range that is, e.g., within 20%, within 10%, within 5%, or within 2% of the given value or range. Any reference signs in the claims should not be construed as limiting the scope.

[1] Peterson, A. I., E.; Schlicht, A., Capability of filling systems to dispense micro-doses of liquid pharmaceutical product. Pharmaceutical Engineering, 2007: p. 1-2

[2] Greb, E. (2010). "Turn Down the Fill Volume." Pharmaceutical Technology

[3] Cromwell, M. E. M., E. Hilario, and F. Jacobson, *Protein aggregation and bioprocessing*. AAPS Journal, 2006. 8(3): p. E572-E579

[4] Thomas, C. R. and D. Geer, Effects of shear on proteins in solution. Biotechnology Letters, 2011. 33(3): p. 443-456

[5] WO2016012567

[6] WO2014048911

The invention claimed is:

1. A dosing system for transferring an aseptic fluid in dosages into a container, comprising:
   a peristaltic pump with a tubing,
   a liquid flow measurement sensor, and
   a control unit,
   wherein the peristaltic pump is configured to provide a filling accuracy of ±3 μL for fill volumes of the aseptic fluid of less than 100 μL by
   the tubing having an internal diameter of between 1.6 mm and 0.8 mm,
   the liquid flow measurement sensor being connected to the peristaltic pump and configured to report a volume of the aseptic fluid passed through the peristaltic pump, wherein the liquid flow measurement sensor is a capacitive pressure sensor, and
   the control unit being coupled to the peristaltic pump and coupled to the liquid flow measurement sensor, wherein the control unit is configured to receive a data signal from the liquid flow measurement sensor, to evaluate the received data signal, and to adapt the peristaltic pump in accordance with the evaluated data signal.

2. The dosing system according to claim 1, wherein the aseptic fluid is a liquid mAbs solution.

3. The dosing system according to claim 1, wherein the filling accuracy is ±1.5 μL for the fill volumes of the aseptic fluid of less than 50 μL.

4. The dosing system according to claim 1, wherein the filling accuracy is ±1.0 μL for the fill volumes of the aseptic fluid of less than 30 μL.

5. The dosing system according to claim 1, wherein the filling accuracy is ±0.5 μL for the fill volumes of the aseptic fluid of less than 20 μL.

6. The dosing system according to claim 1, wherein the filling accuracy is ±0.05 μL for the fill volumes of the aseptic fluid of less than 12 μL.

7. The dosing system according to claim 1, wherein the dosing system comprise surfaces manufactured from a sterilizable material.

8. The dosing system according to claim 1, wherein the aseptic fluid has a viscosity of less than 15 cP±2 cP.

9. The dosing system according to claim 1, wherein the aseptic fluid has a viscosity of 16 cP±1 cP.

10. The dosing system according to claim 1, wherein the aseptic fluid has a viscosity of less than 1500 cP±20 cP.

11. The dosing system according to claim 1, wherein the aseptic fluid has a viscosity of 1480 cP±1 cP.

12. The dosing system according to claim 1, wherein the peristaltic pump comprises a flexible tube, a counter pressure element, a plurality of actors and a drive, wherein
   the flexible tube is arranged along the counter pressure element,
   the actors are moveable by the drive in relation to the flexible tube,
   the flexible tube is compressible between the actors and the counter pressure element by moving the actors,
   the flexible tube is essentially straightly arranged along the counter pressure element thereby forming a longitudinal axis,
   the actors are arranged parallel to each other along the longitudinal axis of the flexible tube, and
   each of the actors is independently and linearly moveable by the drive along an actuation axis essentially perpendicular to the longitudinal axis of the flexible tube from a home position, in which the flexible tube is open for a fluid to pass, to an end position, in which the flexible tube is compressed and sealed.

13. The dosing system of claim 12, wherein the flexible tube of the peristaltic pump is partially pre-compressed between the plurality of actors and the counter pressure element when all actors of the plurality of actors are in their home positions.

14. The dosing system according to claim 1, wherein the adapting of the peristaltic pump comprises adjusting a volume dispensed by the peristaltic pump.

15. A process for controlling the accuracy of the dosing system according to claim 1, wherein a dispensed volume of the aseptic fluid by the peristaltic pump is measured by the capacitive pressure sensor connected to the peristaltic pump for reporting a volume of a fluid passed through the peristaltic pump.

16. The process according to claim 15, wherein the capacitive pressure sensor measures a change of capacitance in an orifice of the capacitor, when a fluid is between electrodes of the capacitive pressure sensor compared to a capacitance of air.

17. The process according to claim 15, wherein the dispensed volume is 50 μL±3 μL and is dispensed according to the following settings:
   6±1 cycles, and
   30 Hz±10 piezo frequency.

18. The process according to claim 15, wherein the dosing system includes a tubing with a wall thickness of 1.6 mm.

19. The process according to claim 15, wherein the peristaltic pump is controlled in accordance with the dispense volume of the fluid reported by the capacitive pressure sensor, wherein controlling the peristaltic pump comprises adjusting a volume dispensed by the peristaltic pump.

20. The process according to claim 15, wherein the dispensed volume is 50 μL±3 μL and is dispensed according to the following settings:
   2±1 cycles, and
   30 Hz±1 piezo frequency.

* * * * *